United States Patent
Faisandier

(10) Patent No.: US 7,020,513 B2
(45) Date of Patent: Mar. 28, 2006

(54) TESTING THE ELECTRICAL CONTINUITY OF THE CONNECTING CABLES FOR A RECORDER OF PHYSIOLOGICAL SIGNALS, IN PARTICULAR A HOLTER RECORDER OF ECG SIGNALS

(75) Inventor: Yves Faisandier, Paris (FR)

(73) Assignee: Ela Medical S.A., Montrouge (FR)

( * ) Notice: Subject to any disclaimer, the term of this patent is extended or adjusted under 35 U.S.C. 154(b) by 516 days.

(21) Appl. No.: 10/351,248

(22) Filed: Jan. 23, 2003

(65) Prior Publication Data

US 2003/0163170 A1  Aug. 28, 2003

(30) Foreign Application Priority Data

Jan. 23, 2002  (FR)  .................................. 02 00817

(51) Int. Cl.
  *A61B 5/04*  (2006.01)
(52) U.S. Cl. ..................... 600/509; 600/547; 607/27
(58) Field of Classification Search ............... 600/508, 600/509, 547, 554; 607/4, 5, 8, 27, 28; 324/508, 324/600, 522, 523, 527, 530
See application file for complete search history.

(56) References Cited

U.S. PATENT DOCUMENTS

| | | | | |
|---|---|---|---|---|
| 4,993,423 A | * | 2/1991 | Stice | 600/509 |
| 5,343,870 A | | 9/1994 | Gallant et al. | 128/711 |
| 5,534,018 A | | 7/1996 | Wahlstrand et al. | 607/27 |
| 5,713,935 A | | 2/1998 | Prutchi et al. | 607/28 |
| 5,755,742 A | * | 5/1998 | Schuelke et al. | 607/27 |
| 5,766,133 A | | 6/1998 | Faisandier | 600/509 |
| 5,921,939 A | * | 7/1999 | Danielsson et al. | 600/509 |
| 6,076,015 A | | 6/2000 | Hartley et al. | 607/20 |
| 6,684,101 B1 | * | 1/2004 | Daum | 600/547 |

FOREIGN PATENT DOCUMENTS

| | | |
|---|---|---|
| EP | 0 182 197 A2 | 5/1986 |
| EP | 0 570 101 A2 | 11/1993 |

* cited by examiner

*Primary Examiner*—Robert E. Pezzuto
*Assistant Examiner*—Brian T. Gedeon
(74) *Attorney, Agent, or Firm*—Orrick Herrington & Sutcliffe LLP

(57) ABSTRACT

Detection of a discontinuity, a disconnection or loss of conductivity, of cables connected to a physiological signal recorder, in particular a Holter recorder of ECG signals by measuring an impedance of the line(s). To measure the impedance of the line comprising the connecting cable connecting an external electrode placed on a patient to a signal terminal (12) of the recorder (10), one generates a current impulse, applies this impulse to the line, measures the variation of voltage resulting on the terminal from the signal during the application duration of the current impulse, and determines the impedance of the line based upon the voltage variations thus measured. The current impulse is a biphasic impulse including two successive cycles of opposite polarities, the durations and the amplitudes of these two cycles being selected so as to define approximately equal respective loads and of contrary signs. A switch (36) connects the base of the pull-down resistance (32) of the signal terminal (12) to the output of a voltage or a current generator (38) during the impedance measurement, and connects it to the potential ground (34) during the remainder of time.

18 Claims, 2 Drawing Sheets

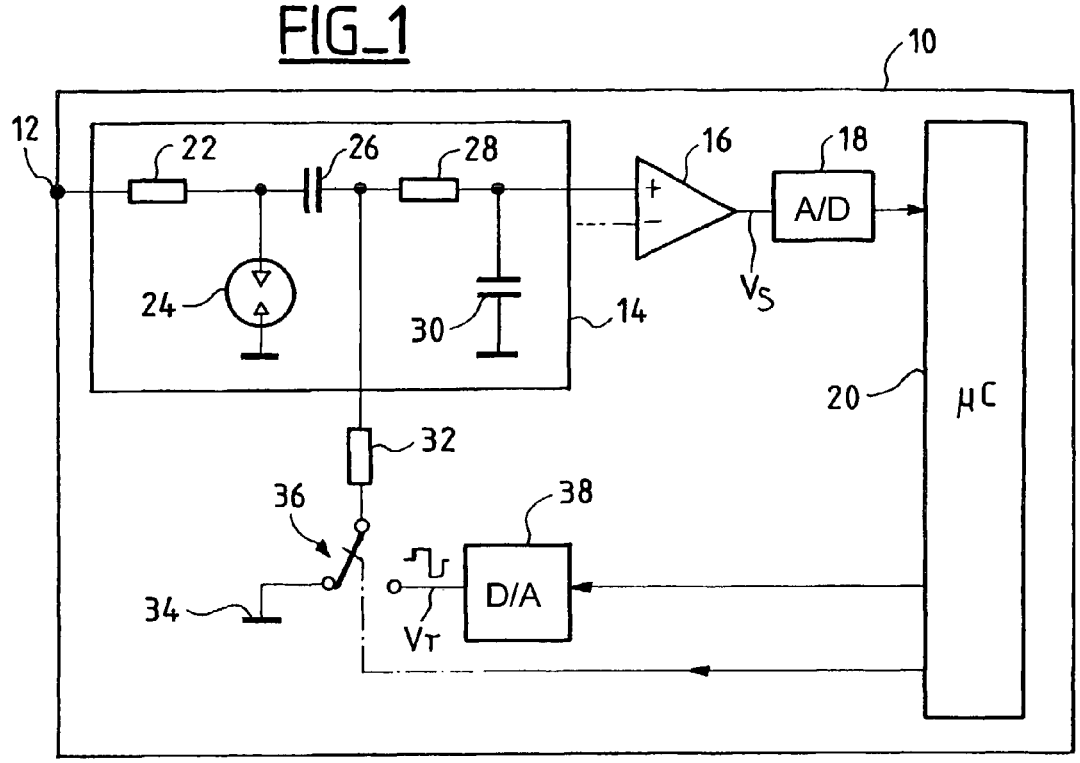
FIG_1
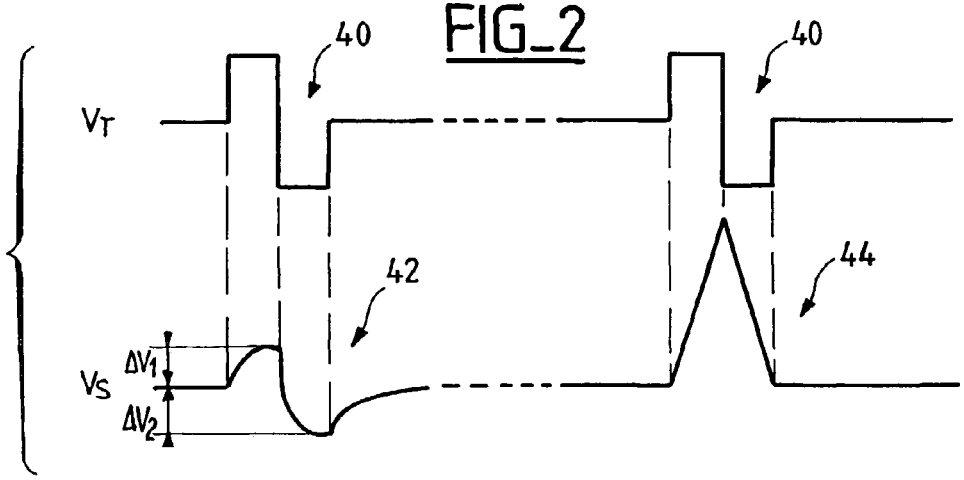
FIG_2
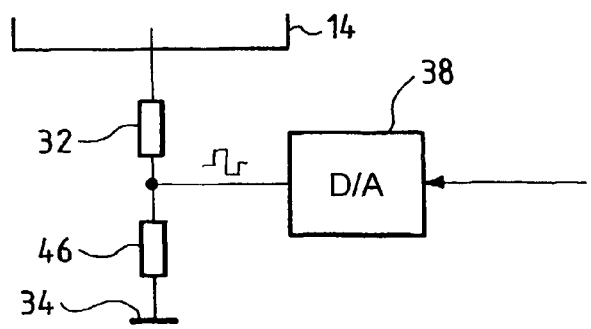
FIG_3

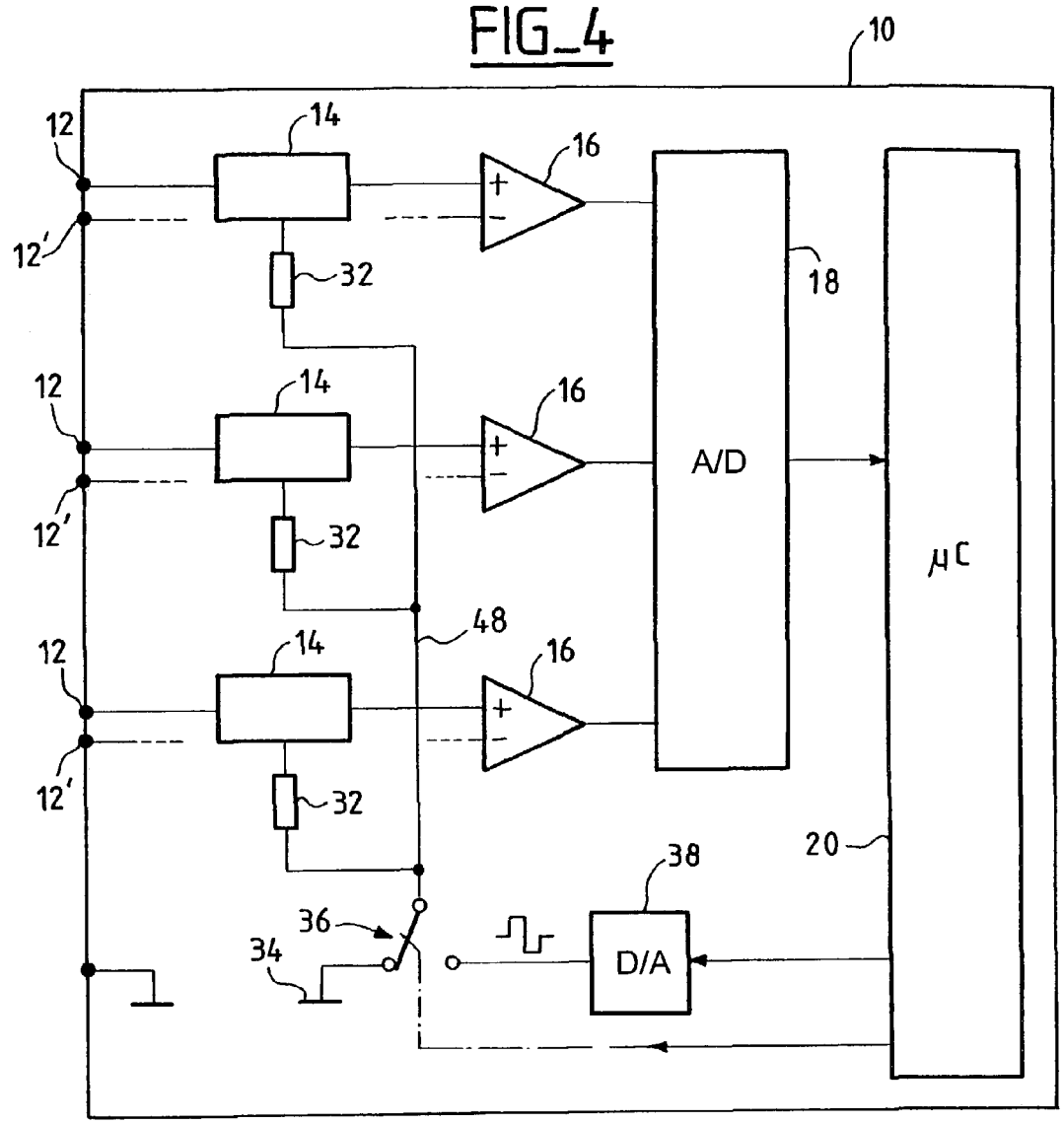
FIG_4
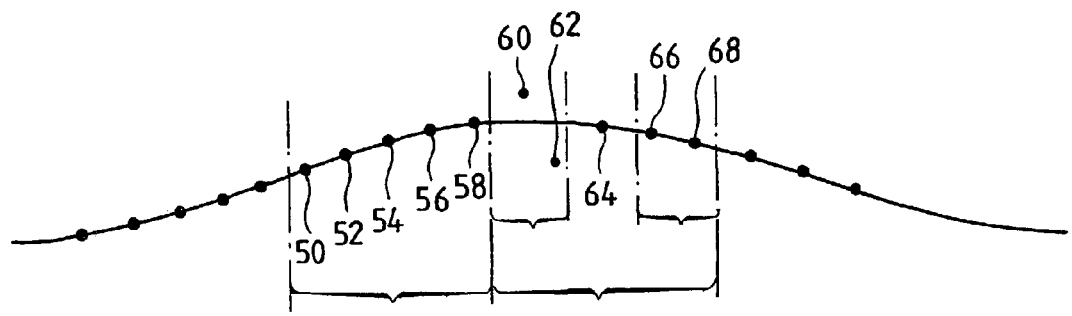
FIG_5

TESTING THE ELECTRICAL CONTINUITY OF THE CONNECTING CABLES FOR A RECORDER OF PHYSIOLOGICAL SIGNALS, IN PARTICULAR A HOLTER RECORDER OF ECG SIGNALS

FIELD OF THE INVENTION

The present invention relates to the recorders of physiological signals, such as the ambulatory recorders of the Holter type ensuring the recording of electrocardiographic ("ECG") signals over a long period of time.

BACKGROUND OF THE INVENTION

Recorders of physiological signals comprise an external case, carried by the patient, to which case one or more sensing electrodes are connected. The sensing electrodes are applied to the body of the patient and connected to the case at a signal input via connecting cables. The connecting cables typically include conductive wire and an insulating sheath. During frequent use, particularly with respect to recorders used for long durations, these cables are subjected to many stresses and end up being degraded. The degradation can go so far as to rupture the electric conductors internal to the cables.

The state of the connecting cables therefore must be monitored. This can be automatically carried out by making an impedance measurement and identifying changes in impedances. It is known, for example, to make such a measurement by injecting a small current on the signal input to which the cable is to be connected (the return path of the current being provided by another measurement electrode or by a ground electrode) and measuring the voltage on the signal input during the current flow. From the measured voltage, one can determine the impedance of the line, to which are added the impedance of the electrodes and the impedance of the body of the patient between the two electrodes included in the current loop.

One can thus highlight any defects of the electric conduction within the cables, as well as any defective connection of the electrodes (e.g., a badly inserted or loose cable or electrode, an internal break, etc.) by thus measuring, in place, the impedance of the line, and, in the case of a Holter recorder, of the lines of the various ECG cables.

The impedance measurement can be carried out not only after installation of the electrodes at the time of putting the device in service, but also throughout the duration of the recording duration: Indeed, it is possible to detect a detachment of an electrode, the disconnection of a cable, etc., and to take account of this defect when recording signals or in the analysis of the acquired signals, or to even ask the patient being monitored to restore continuity by replacing the electrode (or cable) or by replugging a disconnected cable.

The small current used in the impedance measurement is typically a microampere-current ("micro-current") and is preferably of an impulse (pulsitile) nature. This is because a continuous micro-current would be likely to cause a polarization of the electrode-skin couple, and an alternating micro-current would involve a relatively significant consumption of energy because of the high frequency to be used, about 100 KHz, which must be higher than the components of the ECG signal (including the peaks of the stimulation pulses generated by a pacemaker eventually implanted in the patient), and of the signals which must be rejected.

For this reason, the most recent apparatuses, such as the Syneflash and Synesis model recording devices available from Ela Medical, Montrouge, France, implement such an impulse process, in which the device injects a small quantity of current (on the order of a microampere) during a very short time (of about a microsecond) to measure the impedance of a line. The amplifier on which the input is connected amplifies the variation of voltage caused by the injection of this current and retransmits this variation to a digital measurement system (analog/digital converter and microcontroller) which memorizes and processes the impedance data, without (theoretically) deterioration of the collected signal.

This process has been found to present two disadvantages, however, in certain situations. First, in the case when an electrode is disconnected, the voltage level at the input on which the current is injected is parasitized (a situation that results from an illegible signal or an interference at the frequency of the power line), or falls to zero. If the level falls to zero, the device receives in fact on the amplifier the ECG signal of the other electrode. It thus amplifies this other signal in a monopolar mode, i.e., compared to the patient ground, thus giving a signal which seems very correct, although detected as abnormal by the microcontroller. In this situation, the system of current injection presents a major defect due to the fact that the load injected on the line which has a high impedance (because of the break in or disconnection of the cable). This impedance creates a voltage that is maintained for a relatively long time because of the input capacitors of the sensing circuit (these capacitors being useful for the passive filtering of the high frequencies). The sensed ECG signal is then very strongly disturbed by peaks caused with each injection of micro-current.

Second, in the case of a patient carrying a pacemaker, the stimulation pulses (or peaks) produced by the implanted device can obstruct the impedance measurement of the external recorder, in two respects. First, if the stimulation peak occurs at the same time that measurement is taken, it can considerably deform the response and give a false value of the impedance. Second, when the voltage peak caused by the injection of current is significant, it can be wrongly interpreted as a stimulation peak by the recorder.

OBJECTS AND SUMMARY OF THE INVENTION

It is, therefore, an object of the present invention to propose a new mode of testing the electrical continuity of a line by an impulse impedance measurement adapted to long duration recordings of physiological signals that overcomes the various above-mentioned disadvantages.

To this end, the invention proposes an apparatus and a process of for testing the electrical continuity of a line by measuring the impedance of the line, the line having a cable connecting an external electrode placed on a patient to a signal terminal of a recorder of physiological signals, in particular of a Holter recorder of ECG signals, comprising the generation of an impulse of current and application of the impulse to the aforementioned line; the measurement of a voltage variation resulting on the signal terminal during the duration of the current impulse application; and determination of the impedance of the line based upon the voltage variation thus measured.

According to a preferred embodiment of the invention, the current impulse is a biphasic impulse including two successive cycles of opposite polarities, the durations and the amplitudes of these two cycles being selected so as to define approximately equal respective loads of opposite signs.

According to an advantageous embodiment of the invention, measurement of the voltage variation comprises the measurement of the of voltage variation at the end of the first cycle of the current impulse and the end of the second cycle of the current impulse of current, and more particularly the addition of the absolute values of these two variations of voltage.

Preferably, the measurement of the voltage variation is operated in a concomitant manner to the collection of ECG signal. The ECG signal is thus sampled at a frequency producing a plurality of samples per cycle of measurement, with at least two samples for the measurement of the voltage variation at the end of the first current impulse cycle and the end of the second current impulse cycle, and at least one sample being used for the measurement of the level of ECG signal. In this last case, the ECG signal is advantageously sampled at a frequency that produces a plurality of samples for the measurement of the level of the ECG signal, and in which the measurement of the ECG signal is taken by averaging the plurality of samples, in particular at least two samples for the measurement of the variation of voltage at the end of the first cycle and the end of the second cycle of the current impulse, with eventually an intervening sample, and at least one sample usable for the measurement of the level of ECG signal.

When the patient is equipped with an implanted pacemaker, it is further envisaged to include the elimination of the stimulation peaks mixed with the collected ECG signal, either by a preliminary detection of the stimulation peaks and definition of a temporal post-stimulation window during which the measurement of the line impedance will be implemented or by a preliminary memorizing of the voltage variation on the signal terminal during the application duration of the current impulse and subtraction of the memorized variation during the detection of a stimulation peak.

In a preferred implementation, the measurement of the line impedance is advantageously reiterated, and it is then envisaged to have an evaluation and periodical memorizing of an impedance value based upon a plurality of preceding measurements, in particular by determining a median of a number of preceding measurements.

The present invention thus has as one aspect a process employing the aforementioned current impulse injection, voltage measurement, and voltage analysis process as described above, and as another aspect circuitry for implementing these functions. Regarding the apparatus of the latter aspect, the recorder can thus comprise, in particular a voltage or a current generator that is controlled by a microcontroller. The voltage output or the current output of this generator is then applied to the base of a pull-down resistance coupled to ground, in addition to the signal terminal, with means for placing the base of the pull-down resistance at the ground potential at times other than during the periods of application of the current or voltage output of the generator.

The means for placing the base of the pull-down resistance at the ground potential advantageously includes a switch selectively controlled between a state of collection of the ECG signal, where the base of the pull-down resistance is connected to the ground potential, and a state of impedance measurement, where the base of the pull-down resistance is instead connected to the output of the generator.

In an alternative embodiment, the means for placing the pull down resistor at ground potential, can include a resistance interposed between ground potential and the base of the pull-down resistance, such that the current or the voltage output of the generator is forced to a zero value except during the periods when the current impulse is to be applied for the impedance measurement.

In yet another embodiment of the apparatus, the device can comprise a plurality of signal terminals, each one equipped with a respective pull-down resistance, and the voltage or the current output of the generator can be either:

(i) applied simultaneously, either to the positive inputs or to the negative inputs, to the bases of these various pull-down resistances, such that the means for placing the base at ground potential apart from the periods of application being a common means, operating simultaneously on the aforementioned pull-down resistances, or (ii) applied independently to the bases of these various pull-down resistances, the means for placing the base at ground potential apart from the periods of current impulse application comprising a plurality of switches, with one switch for each signal terminal.

BRIEF DESCRIPTION OF THE DRAWINGS

Further benefits, features and characteristics of the present invention will become apparent to a person of ordinary skill in the art in view of the following detailed description of a preferred embodiment of the invention, made with in reference to the annexed drawings, in which like reference characters refer to like elements, and in which:

FIG. 1 is a schematic diagram of the circuits of a recorder in accordance with the present invention;

FIG. 2 illustrates the chronograms of an injected current impulse injected and the resulting collected voltage signal in the case of a correct electric connection and a defective connection;

FIG. 3 is a partial view illustrating an alternative of implementation of a portion of FIG. 1;

FIG. 4 is a generalization of the circuit of FIG. 1 with the simultaneous measurement of the impedances on several inputs; and FIG. 5 illustrates selecting the sampling points of an ECG signal to interpose the impedance measurement while sampling an ECG signal.

DETAILED DESCRIPTION OF THE INVENTION

With reference to FIG. 1, a recorder case 10 is shown, equipped with signal inputs 12, of which only one is represented, there typically being seven inputs 12 in the case of an ECG recording device. Each input is connected to a connecting cable (not represented) the other end of which is connected to a respective electrode applied to a patient to allow for the collection of physiological signals (not shown).

Each signal input 12 has an associated a protection circuit 14 the output of which is connected to an input of a differential amplifier 16. The other input of differential amplifier 16 is connected either to another signal input (for a bipolar measurement) or to a ground potential (for a monopolar measurement).

The output of differential amplifier 16, after conditioning by a conventional high-pass and low-pass filtering circuit (not shown), is converted by an analog/digital converter 18 into a signal that is applied to a microcontroller 20 ensuring the treatment (filtering, compression, recording, etc.) of the collected signal as well as that of the collected signals from the other electrodes placed on the patient (e.g., using a multiplexor, not illustrated), by software controlled signal processing techniques.

The protection circuit 14 comprises a serial resistance 22, about 100 KΩ, intended to limit the current circulating in the cable and via the electrode. A spark-gap component 24 ensures a limitation in voltage at the input, about 40 V, to take into account, in particular, the defibrillation shocks to be applied to the patient, so that the latter do not destroy the input circuits of the recorder. A suitable spark-gap component is the device sold by Cooper Electronics under the tradename SURGIX. The protection circuit 14 also comprises a connection capacitor 26 to block any possible continuous current (DC) component, as well as an RC network 28, 30 to filter the highest frequencies presented to differential amplifier 16.

Each input 12 is also equipped with a pull-down resistor 32 connected to the ground 34, of high value (typically about 10 MΩ), mounted between the signal line, on the one hand, and ground 34, on the other hand.

For the impedance measurement, the invention proposes, instead of a permanent connection to the ground of pull-down resistance 32, to connect the base of resistance 32 to a switch 36 that operates to connect the base either to ground 34 (the normal position for physiological signal acquisition) or to a generator of voltage or of current 38 (during the impedance measurement). The commutation (switching) is operated under the control of microcontroller 20. For practical reasons, it is generally simpler to use a voltage generator for generator 38, which devices are often available on conventional microcontrollers in the form of a digital to analog converter (D/A).

More preferably, for the impedance measurement generator 38 provides, during a first cycle of short duration, for example, 1 ms, a voltage $V_T$ of a certain polarity. Then, during a second cycle of the same duration, a voltage of opposite polarity (cf the first line of the chronogram of FIG. 2, where the shape of the corresponding signal is illustrated at 40). This inversion of the polarities makes it possible to cancel the loads in the line, so that the measurement of the ECG signal will not be disturbed any more, even with a high line impedance, for example, because of a disconnected electrode.

The relative amplitude of the positive and negative pulses of impulse 40 can be possibly optimized, by a learning mode wherein the microcontroller 20 learns to compensate for the shift caused by an absence of a cable, i.e. to compensate for the shift introduced by the measuring circuit, so as to adjust the return of the resulting signal to the base line signal in the absence of a cable, this adjustment being obtained by introducing a small dissymmetry between the two impulse cycles to compensate for the various shifts that are likely to be introduced into the measuring circuit.

The value of the impedance is calculated based upon the voltage variations $V_S$ measured at the output of the amplifier 16 at the end of the first cycle (variation $\Delta V_1$) and at the end of the second cycle (variation $\Delta V_2$). The measured signal $V_S$ is illustrated into area 42 on the second line of the chronogram of FIG. 2, in the normal case, i.e. a not disconnected electrode or an intact connection wire. The voltage peak caused by the double injection of current has in this case an amplitude proportional to the impedance, and the variations of voltage $\Delta V_1$ and $\Delta V_2$ are in absolute value approximately equal, taking in account the errors of dissymmetry.

To optimize the calculation of the impedance, it is possible to add the absolute values of the voltage variations $\Delta V_1$ and $\Delta V_2$: As explained below in connection with FIG. 5, when the ECG signal is not null, it locally presents variations comparable to a slope which, if it is considered that the latter is stable over the short period of the impedance measurement, modifies the two values $\Delta V_1$ and $\Delta V_2$ in opposite directions; the total of these two values thus remains stable. In the case of a high impedance, corresponding to a situation of a disconnected or discontinuous (broken) cable, or of a disconnected electrode (i.e., one not properly coupled to the patient), the response to the current impulse 40 is very appreciably modified, as illustrated at area 44 on the second chronogram of FIG. 2: the load injected on the line with high impedance at the time of the first cycle of the current impulse 40 creates a high voltage, one that the microcontroller can immediately detect. In addition, injection of current in the opposite direction at the time of second cycle of current impulse 40 will cause cancellation of loads stored in the various input capacitors (loads that did not flow out (discharge) because of the high impedance between the signal terminal and the ground), thus allowing the return of the signal to the base line. That causes to place the entire system, from the point of view of the electric charges, in its former state.

The impedance measurement is preferably determined by microcontroller 20 at regular intervals, for example, several times per minute, or even several times per second.

The impedance measurement will take into account the various components of the protection circuit 14 against high and low frequency interference. In this regard, the components do not obstruct the impedance measurements, but they must be taken into account in the measurements. Thus, serial resistance 22 placed at input 12 to limit the current that can circulate in the line when a high voltage is applied to an electrode, for example, in the case of a defibrillation shock, comes to be added to the impedance measurement. As for capacitor 26 charged to cutoff the very low frequencies, it does not intervene in calculation owing to the fact that it completely transmits the measurement current to the line. Moreover, it has the advantage of removing possible DC components that are likely to decrease the precision of the signal injected by generator 38.

To make the measurement impedance reliable, the recorder must avoid taking into account aberrant values. For that, it can practice several successive measurements and then keep only one of them, for example, employ an average or a median of a plurality of measurements taken. By this technique one thus eliminates from the risk of recording an aberrant measurement if, for example, a high frequency artifact appears during the impedance measurement cycle. For one example, if the device takes ten measurements during a one minute interval, it can record each minute a median value of these ten measurements: the value of the impedance is thus updated once per minute.

Various alternatives and improvements of the process of the invention can be considered. For example, it is possible to test simultaneously two lines by using signals that are opposite in phase. The current will circulate between the two electrodes, and this minimizes any risk of false measurement if the ground electrode becomes disconnected (the final balance of loads reminds null).

In an alternative embodiment, as illustrated in FIG. 3, it is possible to remove switch 36, leave generator 38 permanently connected to the base of resistance 32, and interpose a resistance 46 between resistance 32 and ground 34. In this embodiment, between the phases of measurement, instead of switching the switch 36 to connect resistance 32 to ground 34 as in the preceding embodiment, microcontroller 20 imposes on generator 38 a zero output voltage, which is equivalent to putting the base of resistor 32 to ground potential. This solution, which is purely static, makes it possible to avoid recourse to using a controlled switch 36; it however presents the disadvantage of requiring a permanent operation of the generator 38, which thus always consumes a certain current because of the resistance network employed. The embodiment of FIG. 1 by contrast, differs in that use of switch 36 makes it possible to completely stop generator 38 except during the impedance measurement, thus making for an economy of the power supply of generator 38.

In addition, it is possible to carry out the impedance measurement on several amplifiers 16 simultaneously. Thus, as illustrated in FIG. 4, recorder 10 typically comprises a plurality of inputs 12, each one connected, via a corresponding plurality of protection circuits 14, to the positive input of a respective amplifier 16. In the same way, inputs 12' are respectively connected to the negative input of these same amplifiers 16. Each positive input 12 is connected by its respective base resistance 32, via a common trunk 48, with a single switch 36 (or alternatively a single resistance 46, as in the case of the embodiment of FIG. 3). In the same way, the negative inputs are connected to another common switch (not shown). The lines are thus tested alternately, positive inputs first, and then negative inputs, for example.

Because the impedance measurement is realized during a very short time period, it is possible to carry out this measurement without stopping the collection of an ECG signal. FIG. 5 illustrates the corresponding manner of proceeding. To be able to measure the impedance, it is necessary to have an amplifier having a sufficiently short time-constant in regard to the measurement cycles. This constant must in particular be shorter than that which is usually used for a sampling at 200 $s^{-1}$ (that is to say approximately 10 ms).

The invention therefore proposes to associate a shorter time-constant, for example, 2 ms instead of 10 ms, with a faster sampling cycle, for example, 1 KHz, by averaging the signal over several points. FIG. 5 illustrates an ECG signal with the various points of sequential sampling such as 50 ... 58 and 60 ... 68. The value of the ECG signal is obtained by averaging five points of sequential sampling 50, 52, 54, 56 and 58. The samples being digitized each millisecond, this operation gives 1000/5=200 points a second (a frequency that is an acquisition frequency value usually used in the existing recorders, which allow for sampling frequencies generally ranging between 128 and 256 Hz).

At the time of an impedance measurement, the injection of the biphasic current impulse will result in two points of sampling 60 and 62 deviating from the base line, and corresponding to amplitudes $\Delta V_1$ and $\Delta V_2$ of the signal in response, as illustrated in FIG. 2. These two data sample points 60 and 62 will be used for the impedance measurement and, on the five successive samples, there will remain at least two sample points 66, 68 to deliver a value of the ECG signal (sample point 64 which follows immediately sample points 60 and 62 is not preserved for the calculation of the average value, by precaution). So the determination of the ECG signal will not be, or at least will be very little, modified during the impedance measurement phase. The only difference being that during this particular cycle the evaluation of the ECG signal will be done by averaging only two points, instead of five in the normal case—but the measurement of the ECG signal will not be stopped, even during only one cycle, due to the impedance measurement.

This manner of proceeding is of course not restrictive, and other alternatives can be considered, for example, the measurement of a number of data points (e.g., three or four points) per cycle, instead of five, by retaining only the last point as value of the ECG signal in the case of a cycle including an impedance measurement, by using different sampling frequencies, etc.

One now will consider the particular case of a patient carrying a pacemaker. In this case, the peaks of stimulation emitted by the pacemaker disturb the operation of the impedance measurement by the recorder. Indeed, these peaks are of an amplitude and a duration of the same order of magnitude as the voltage variations related to the measurement of impedance; the measuring circuit can thus confuse the signal collected during the impedance measurement (e.g., the signal illustrated on the second line of FIG. 2) with a stimulation peak. Until now, this difficulty was circumvented by removing any impedance measurement in the recorders carried by patients equipped with a pacemaker.

The invention proposes to resolve this difficulty, by proposing two methods authorizing impedance measurements by the recorder even when the patient carries a pacemaker. The first method concerns synchronizing the impedance measurement cycle on the recognized stimulation peaks. For that, the recorder seeks the presence of peaks (analyzing signals at 1000 Hz by use of software or a specific peak detecting circuit), and delivers temporal windows placed after the peaks (for example, 10 ms), during which it will be confident that the pacemaker will not emit other stimulation pulses. When the recorder wants to take the impedance measurement, it awaits a window of measurement and performs the measurement as previously described, without being likely to be disturbed. If no peak is detected in the ECG signal for one relatively significant length of time (e.g., a few seconds), the recorder considers that the pacemaker is in an inhibited mode (the so-called "demand" mode) and that it can thus launch its measurement of impedance; there remains however a risk (low) to be in synchronism with a peak, if a stimulation starts at this time.

The second method concerns rebuilding the signal at 1000 Hz: during a first measurement, the response to the current impulse is memorized. Under normal operation, with each impedance measurement, the ECG signal is collected and, using a subtraction algorithm, the previously recorded first measurement response is removed from the detected signal. One thus obtains a signal free of the impedance measurement artifacts, and on which one can seek the stimulation peaks (the proper response at the injection of the measurement signal is obtained starting from the preceding cycles, and eventually the following cycles).

Known devices where the invention might be practiced have been cited in the present disclosure, namely the Syneflash™ and Synesis™ devices available from ELA Medical. Circuits for implementing the aforementioned functions for controlling the generator output and operating switches are known to persons of ordinary skill in the art. Similarly, software suitable for operating the microcontroller to in turn operate the switches, generator and temporal window, as well as analog to digital and digital to analog converters, are believed to be within the abilities of a person of ordinary skill in the art to prepare and implement.

One skilled in the art will appreciate that the present invention can be practiced by other than the described embodiments, which are presented for purposes of illustration and not of limitation.

I claim:

1. A process for testing the electrical continuity of a line by measuring an impedance of a line, the line comprising a connecting cable connecting an external electrode placed on a patient to a signal terminal of a recorder of physiological signals comprising the steps of:

generating a biphasic current impulse having a first cycle of a first polarity and a second cycle of a second polarity, each cycle having a duration and an amplitude, selecting said durations and the amplitudes of said first and second cycles to define approximately equal respective loads of contrary signs on said line;

applying said impulse to said line.

measuring a voltage variation on the signal terminal in response to said biphasic current impulse; and determining an impedance of the line based upon said measured voltage variations.

2. The process of claim 1, wherein measuring the voltage variation comprises measuring a first voltage variation at the end of said first cycle and measuring a second voltage variation at the end of said second cycle.

3. The process of claim 2, wherein measuring the voltage variation further comprises obtaining an absolute value of the voltage variations measured at the end of the first cycle and at the end of second cycle and adding them together.

4. The process of claim 2, further comprising using said line to collect an ECG signal, sampling the collected ECG signal at a first frequency and obtaining a plurality of samples in a first measurement cycle, measuring the ECG signal using at least one of said samples, wherein measuring said voltage variation further comprises using at least two of said samples for the measurement of the voltage variations at the end of the first cycle and the end of the second cycle.

5. The process of claim 4, wherein measuring the ECG signal further comprises averaging selected ones of said plurality of samples.

6. The process of claim 4, further comprising selecting said first frequency of sampling the ECG signal to produce at least two samples for use in the measurement of the voltage variation at the end of each of the first cycle and the second cycle, and at least one sample for use in the measurement of the ECG signal.

7. The process of claim 6, wherein selecting said first frequency further produces an intervening sample following said at least two samples used in the voltage variation measurement, wherein said intervening sample is not used in measurement of said voltage variations.

8. The process of claim 1, wherein the patient is equipped with an implanted pacemaker able to deliver stimulation pulses, further comprising eliminating from the measured voltage variations signals corresponding to said stimulation pulses.

9. The process of claim 8, wherein eliminating signals corresponding to said stimulation pulses comprises detecting a stimulation pulse in the measured voltage variation, defining a temporal post-stimulation window, and measuring the impedance of said line during said window.

10. The process of claim 8, wherein eliminating signals corresponding to said stimulation pulses further comprises memorizing voltage variations on the signal terminal during the application of the current impulse, and subtracting said memorized variations during the detection of a stimulation pulse.

11. The process of claim 1, further comprising reiterating the measurement of line impedance, and memorizing periodically a value of impedance based upon a plurality of line impedance measurements.

12. The process of claim 11, wherein periodically memorizing the value of impedance further comprises calculating a median of said plurality of line impedance measurements.

13. Apparatus for recording physiological signals comprising a signal terminal, a line comprising a cable connecting an external electrode placed on a patient to the signal terminal, and means for testing a continuity of a line by measuring an impedance of said line including:

means for generating a biphasic current impulse and applying said impulse to said line, said biphasic current impulse including two successive cycles of opposite polarities, each cycle having a duration and an amplitude wherein the durations and the amplitudes are selected to define approximately equal respective loads of contrary signs;

means for measuring a voltage variation resulting on the signal terminal during the application of the biphasic current impulse; and means for determining an impedance of the line based upon said measured voltage variation.

14. The apparatus of claim 13, further comprising a microcontroller, wherein the means for measuring the line impedance further comprises a ground potential and a pull down resistance having a base, wherein the impulse generating means comprises one of a voltage generator having a voltage output and a current generator having a current output, said microcontroller controlling said one generator so that the one voltage or current output applied to the base of a pull-down resistance is coupled to said ground and signal terminal, and means for placing at the ground potential the base of the pull-down resistance apart from during application of the biphasic current impulse.

15. The apparatus of claim 14, wherein the means for placing at ground potential the base of the pull-down resistance apart from the periods of application of the current or voltage output of the one generator comprises a switch selectively controlled between a first state, wherein the base of the pull-down resistance is connected to the ground potential for collecting an ECG signal, and a second state, wherein the base of the pull-down resistance is connected to the generator output for impedance measuring.

16. The apparatus of claim 14, wherein the means for placing at ground potential the base of the pull-down resistance apart from the periods of application of the current or voltage output of the one generator comprises a resistance inserted between the ground potential and the base of the pull-down resistance, wherein the current or the voltage output of the one generator is forced to a zero value other than during application of the biphasic current pulse.

17. The apparatus of claim 14, comprising a plurality of signal terminals having a corresponding plurality of pull-down resistances, wherein the voltage or the current output of the one generator is applied simultaneously at the bases of said plurality of pull-down resistances, and wherein the means for placing to the ground potential the base of the pull-down resistances apart from the periods of biphasic current impulse application further comprise means for placing at ground potential the bases of said plurality of pull-down resistances essentially simultaneously.

18. The apparatus of claim 14, comprising a plurality of signal terminals having a corresponding plurality of respective pull-down resistances, wherein the voltage output or the current output of the one generator is applied independently to the bases of the plurality of pull-down resistances, and wherein the means for placing at ground potential the base of said pull-down resistance apart from the periods of application further comprises a plurality of switches, operated under microcontroller control, said plurality of switches corresponding to said plurality of terminals.

* * * * *